US008597367B2

(12) United States Patent
Dillinger

(10) Patent No.: US 8,597,367 B2
(45) Date of Patent: Dec. 3, 2013

(54) PARTIALLY SOLUBLE IMPLANTABLE OR INSERTABLE MEDICAL DEVICES

(75) Inventor: Norman Dillinger, Ellettsville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/242,746

(22) Filed: Sep. 23, 2011

(65) Prior Publication Data

US 2012/0010721 A1 Jan. 12, 2012

Related U.S. Application Data

(63) Continuation of application No. 11/454,671, filed on Jun. 16, 2006, now Pat. No. 8,048,168.

(51) Int. Cl.
*A61F 2/04* (2013.01)

(52) U.S. Cl.
USPC ........................................ 623/23.7

(58) Field of Classification Search
USPC .................. 623/23.7; 604/502, 891.1
See application file for complete search history.

(56) References Cited

U.S. PATENT DOCUMENTS

| | | | |
|---|---|---|---|
| 4,946,899 A | 8/1990 | Kennedy et al. | |
| 5,622,665 A | 4/1997 | Wang | |
| 5,741,331 A | 4/1998 | Pinchuk | |
| 5,741,429 A | 4/1998 | Donadio et al. | |
| 6,273,913 B1 | 8/2001 | Wright et al. | |
| 6,368,356 B1 | 4/2002 | Zhong et al. | |
| 6,508,805 B1 | 1/2003 | Garabedian et al. | |
| 6,545,097 B2 | 4/2003 | Pinchuk et al. | |
| 6,709,451 B1 | 3/2004 | Noble et al. | |
| 7,699,886 B2 | 4/2010 | Sugimoto | |
| 2002/0035395 A1 | 3/2002 | Sugimoto | |
| 2002/0082679 A1 | 6/2002 | Sirhan et al. | |
| 2002/0107330 A1 | 8/2002 | Pinchuk et al. | |
| 2003/0004564 A1* | 1/2003 | Elkins et al. ................. | 623/1.15 |
| 2003/0040789 A1* | 2/2003 | Colgan et al. ................ | 623/1.11 |
| 2003/0135265 A1 | 7/2003 | Stinson | |
| 2003/0153983 A1 | 8/2003 | Miller et al. | |
| 2003/0224033 A1 | 12/2003 | Li et al. | |
| 2004/0116999 A1 | 6/2004 | Ledrgerber | |
| 2004/0181275 A1 | 9/2004 | Nobel et al. | |
| 2004/0220660 A1 | 11/2004 | Shanley et al. | |
| 2004/0243225 A1 | 12/2004 | Ragheb et al. | |
| 2004/0249441 A1 | 12/2004 | Miller et al. | |
| 2005/0070996 A1* | 3/2005 | Dinh et al. ................... | 623/1.42 |

FOREIGN PATENT DOCUMENTS

| | | |
|---|---|---|
| EP | 0706784 A1 | 4/1996 |
| EP | 0747069 A2 | 12/1996 |
| WO | 93/04722 | 3/1993 |
| WO | 9823228 | 6/1998 |
| WO | 0247581 | 6/2002 |

OTHER PUBLICATIONS

Young, S.; et al., "In-Stent restenosis limitation with stent-based controlled-release nitric oxide: initial results in rabbits." Radiology (2004); 230:377.

Lam, J.S.; et al. "Update on ureteral stents." Urology 64: 9-15 (2004).

\* cited by examiner

*Primary Examiner* — Kevin C Sirmons
*Assistant Examiner* — Brandy S Lee
(74) *Attorney, Agent, or Firm* — Mayer & Williams PC; David B. Bonham

(57) ABSTRACT

An elongate medical device configured for at least partial implantation or insertion into a subject. The medical device has at least one surface that contains one or more depressions, which are at least partially filled with a soluble material. Also described methods of making such devices.

30 Claims, 7 Drawing Sheets

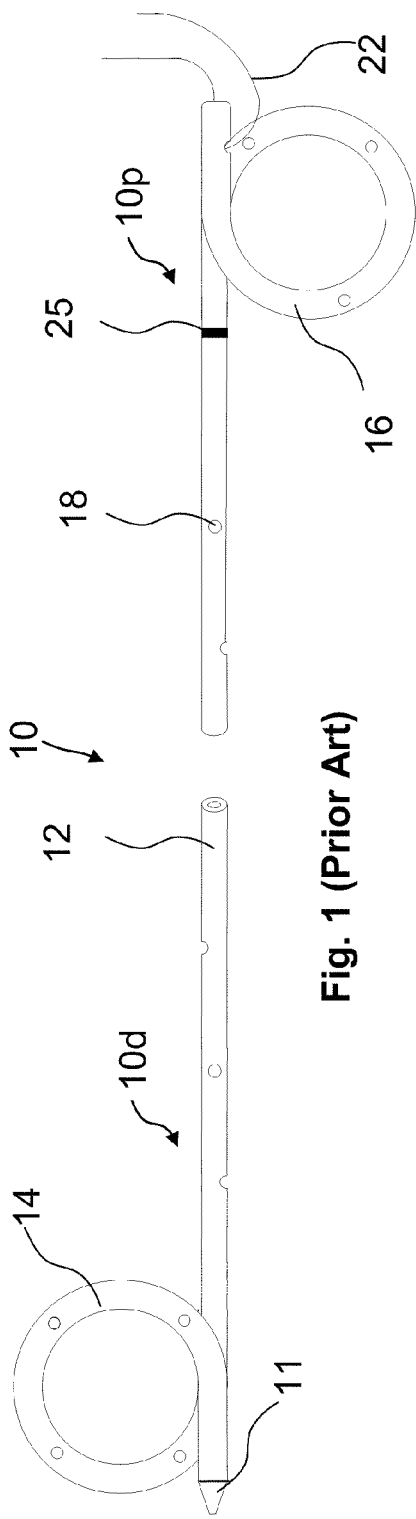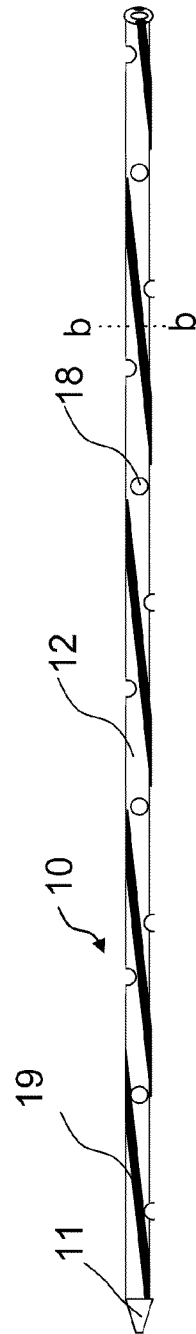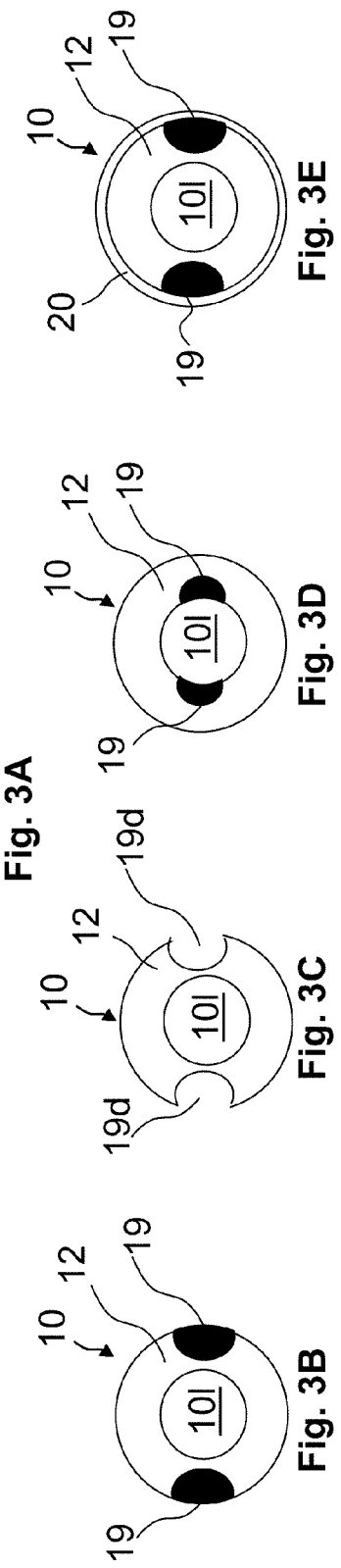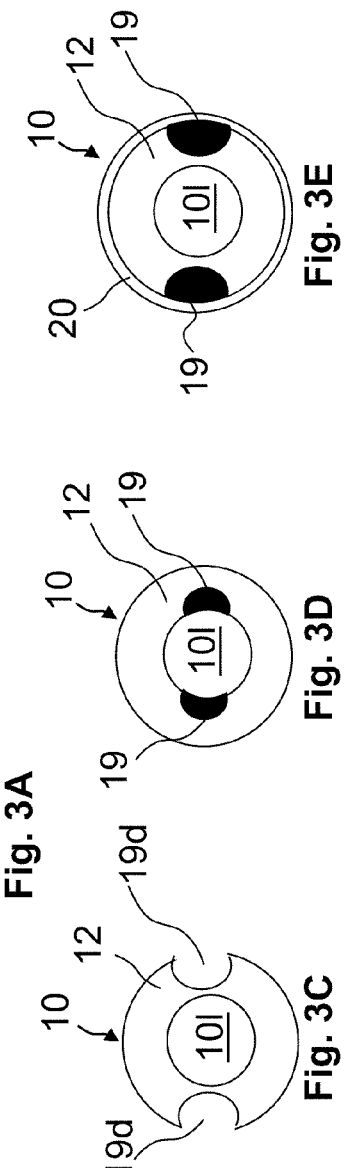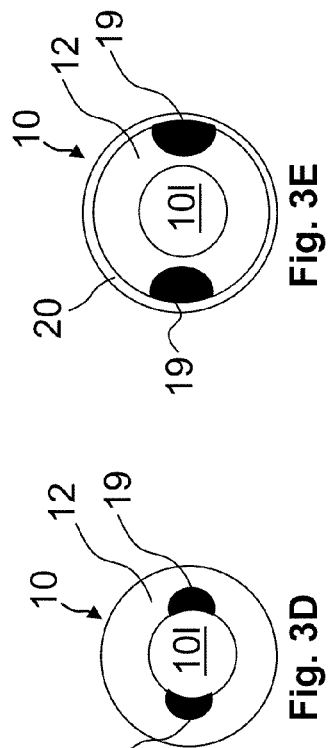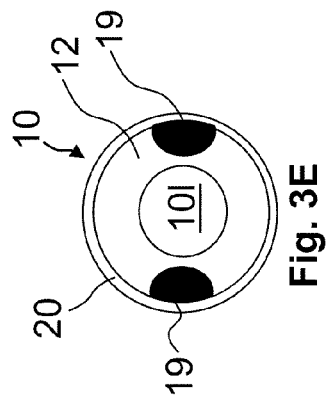

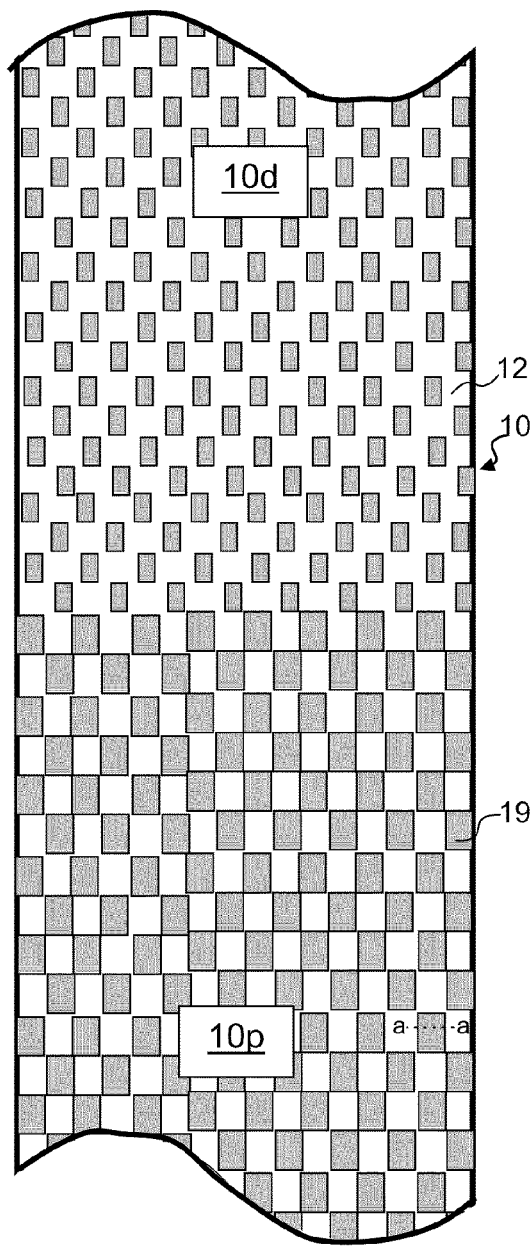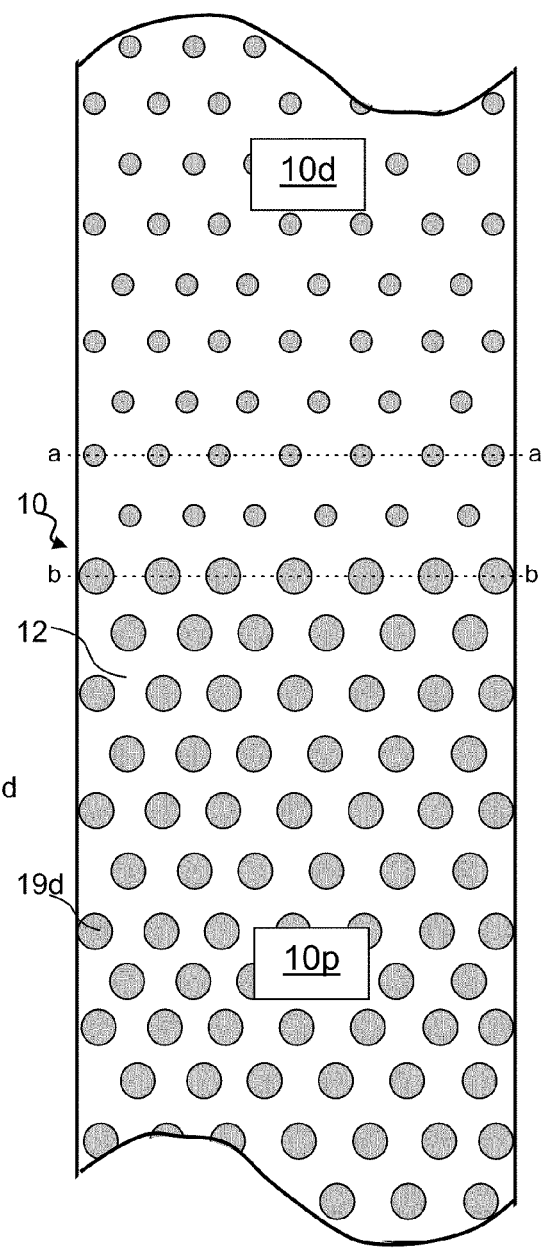
Fig. 9
Fig. 10A

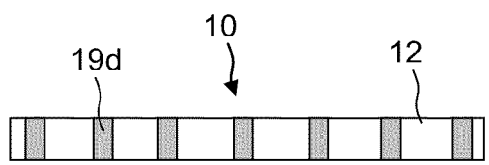
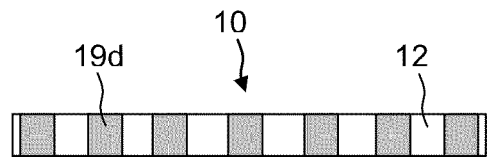
Fig. 10B         Fig. 10C
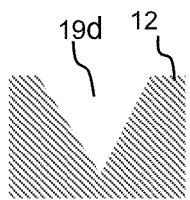
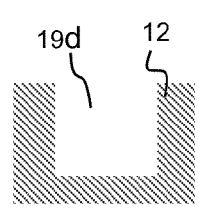
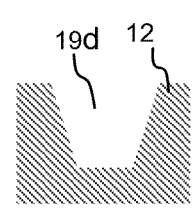
Fig. 11A         Fig. 11B         Fig. 11C
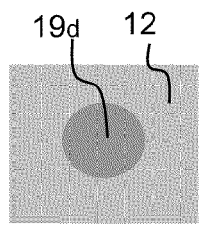
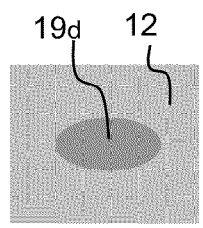
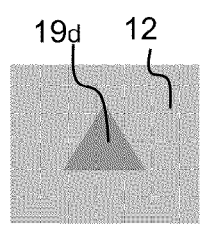
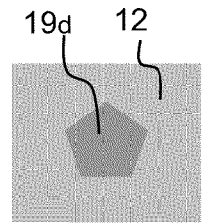
Fig. 12A         Fig. 12B         Fig. 12C         Fig. 12D

PARTIALLY SOLUBLE IMPLANTABLE OR INSERTABLE MEDICAL DEVICES

STATEMENT OF RELATED APPLICATION

This application is a continuation of U.S. Ser. No. 11/454,671, filed Jun. 16, 2006 entitled "PARTIALLY SOLUBLE IMPLANTABLE OR INSERTABLE MEDICAL DEVICES", which is incorporated by reference herein in its entirety.

TECHNICAL FIELD

This invention relates to medical devices, and more particularly to partially soluble implantable or insertable medical devices and methods for their manufacture.

BACKGROUND INFORMATION

Numerous medical devices have been developed for implantation or insertion into patients. Unfortunately, many such medical devices are commonly associated with patient discomfort or pain after being positioned within the patient. As a specific example, ethylene vinyl acetate (EVA) copolymer based ureteral stents are widely used to facilitate drainage in the upper urinary tract (e.g., drainage from the kidney to the bladder), for example, following ureteroscopy, endoureterotomies, and endopyelotomy for ureteral strictures, as well as in other instances where ureteral obstruction may occur.

A schematic diagram of an exemplary stent 10 of this type is illustrated in FIG. 1. The stent 10 has a proximal end 10p and a distal end 10d. It is a tubular polymer extrusion having a shaft 12, a distal renal retention structure (e.g., renal "pigtail" 14), and a proximal retention structure (e.g., bladder "pigtail" 16). These retention structures prevent upward migration of the stent toward the kidney or downward migration of the stent toward the bladder. Other examples of retention structures for use in ureteral stents include, for example, spirals, coils, corkscrews, mallincotts, barbs, mushrooms and hook ends, among others. Once properly deployed in the ureter, the stent 10 provides ureteral rigidity and allows the passage of urine.

The stent 10, as exemplified by FIG. 1, may further be provided with any one or more of the following: (a) a tapered tip 11, to aid insertion, (b) multiple side ports 18 (one numbered), which are typically arranged in a spiral pattern down the length of the body to promote drainage, (c) graduation marks 25 (one illustrated), which are normally used for visualization by the physician to know when the appropriate length of stent has been inserted into the ureter, and (d) a suture 22, which aids in positioning and withdrawal of the stent, as is known in that art.

During placement, such ureteral stents 10 are typically placed over a urology guide wire, through a cystoscope and advanced into position with a positioner. Once the proximal end of the stent is advanced into the kidney/renal calyx, the guide wire is removed, allowing the pigtails 14, 16 to form in the kidney 19 and bladder 20, as shown in FIG. 2. The renal pigtail 14 of the stent may be closed or tapered, depending on the method of insertion (e.g., the use of a guide wire or otherwise). As shown in FIG. 2, the stent 10 extends through the ureteral orifice 21a and into the bladder 20. For clarity, the ureter entering bladder 20 through the opposite ureteral orifice 21b is not shown.

Such stents are known, however, to be associated with a degree of pain and/or discomfort, particularly in the bladder and flank area after insertion. One way of addressing this pain is to use a softer material, particularly in forming the proximal end of the stent, which engages more sensitive tissue. Stents of this type may employ co-extrusion to combine a firm durometer EVA copolymer at the distal end, which improves stent advancement, and a soft durometer EVA at the proximal end, which improves comfort. A specific example of such a stent is the Polaris™ Dual Durometer Percuflex® Ureteral Stent with HydroPlus™ Coating, available from Boston Scientific, Natick, Mass., USA.

Other ways of addressing pain and discomfort include providing systemically administered painkillers or providing devices which release painkillers locally. See, e.g., U.S. Pat. App. Pub. No. 2003/0224033 entitled "Implantable or insertable medical devices for controlled drug delivery."

Another issue associated with ureteral stents is the formation of encrustation in vivo, which may be addressed, for example, through the use of devices that release antimicrobial compounds locally. In this regard, see, e.g., U.S. Pat. App. Pub. No. 2004/0249441 entitled "Implantable or insertable medical device resistant to microbial growth and biofilm formation."

SUMMARY OF THE INVENTION

According to one aspect of the present invention, an elongate medical device is provided, which is configured for at least partial implantation or insertion into a subject. The medical device has at least one surface that contains one or more depressions, which are at least partially filled with a soluble material.

One advantage of the present invention is that implantable or insertable medical devices may be provided, which are initially relatively stiff, improving implantation or insertion, but which become more flexible over time, minimizing pain and discomfort after implantation or insertion.

Another advantage of the present invention is that implantable or insertable medical devices may be provided, which develop channels, through-holes, or other depressions after implantation or insertion, thereby improving flow around and/or through the devices.

These and other embodiments and advantages of the present invention will become immediately apparent to those of ordinary skill in the art upon review of the Detailed Description and Claims to follow.

BRIEF DESCRIPTION OF THE DRAWINGS

FIG. 1 is a schematic representation of a ureteral stent, according to the prior art.

FIG. 3A is a schematic side view of the distal end of a ureteral stent, in accordance with an embodiment of the invention.

FIG. 3B is a schematic cross-sectional view taken along line b-b of FIG. 3A, in accordance with an embodiment of the invention.

FIG. 3C is a schematic cross-sectional view taken along line b-b of FIG. 3A after implantation and dissolution of soluble material.

FIGS. 3D-3E are schematic cross-sectional view taken along line b-b of FIG. 3A, in accordance with two alternative embodiments of the invention.

FIGS. 6-10A are each schematic flat views of the exterior of a portion of the length of a ureteral stent, in accordance with various other embodiments of the invention.

FIGS. 10B and 10C are schematic cross-sectional views taken along lines a-a and b-b of FIG. 10A, respectively, in accordance with an embodiment of the invention.

FIGS. 11A-11C are schematic cross-sectional views illustrating various depression configurations, in accordance with various embodiments of the invention.

FIGS. 12A-12D are schematic top views illustrating various depression configurations, in accordance with various embodiments of the invention.

DETAILED DESCRIPTION OF THE INVENTION

Figure 2:
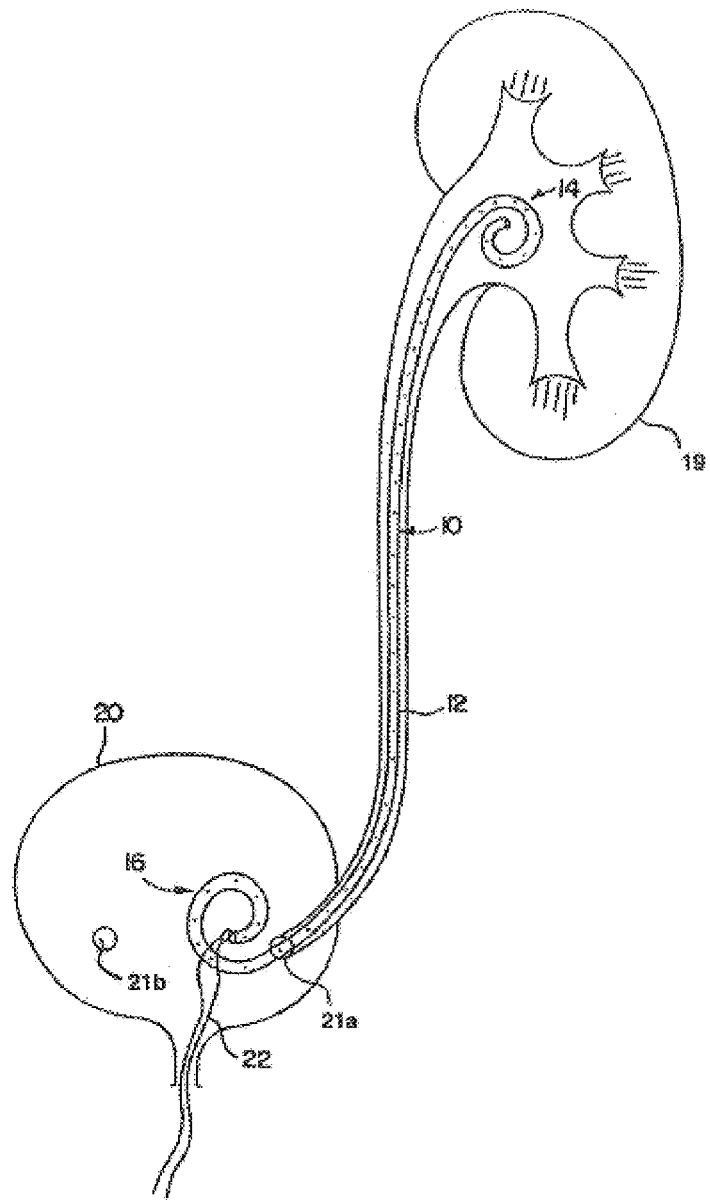
FIG. 2 shows the ureteral stent of FIG. 1 as positioned within the body.

In one aspect, the present invention is directed to implantable or insertable medical devices that comprise an elongate body, at least one surface of which contains one or more depressions that are filled with a soluble material. Such devices are particularly well suited for implantation or insertion at sites associated with pain or discomfort subsequent to implantation or insertion.

One specific embodiment of the invention will now be described in conjunction with FIGS. 3A and 3B, which are schematic side and cross-sectional views of the distal end of a ureteral stent 10. Ureteral stents are typically used to facilitate urinary drainage from the kidney to the bladder in patients having a ureteral obstruction or injury, or to protect the integrity of the ureter during a variety of surgical manipulations. They are used, for example, in post endo-urological procedures to act as a scaffold in the event of ureteral obstruction secondary to the procedure. Stents are also used as palliative devices to provide patency in the presence of congenital defects, strictures or malignancies that may cause ureter obstructions.

The stent 10 of FIGS. 3A-3B is similar to that of FIG. 1 in that it has a tubular body 12 with a plurality of side ports 18 (one numbered), which are arranged in a spiral pattern down the length of the body, and a tapered tip 11. However, unlike the stent 10 of FIG. 1, the stent 10 shown contains a pair of depressions (channels, in this embodiment), also arranged in a spiral pattern down the length of the body, which are filled with a soluble material 19.

Upon implantation or insertion into a subject, the soluble material 19 dissolves, leaving behind depressions 19d (see, e.g., the schematic cross-section of FIG. 3C). As can be seen by comparing FIGS. 3B and 3C, one effect of the removal of the material 19 is a reduction in the solid cross-section area of the device (i.e., regions which previously contained a solid soluble material 19 become depressions 19d). This reduction in the solid cross-sectional area may, in turn, increase the flexibility of device and thus patient comfort.

For this reason, it is beneficial in various embodiments of the invention, to provide a material 19 that dissolves (or at the very least softens) over a relatively short time period, for example, ranging from less than 1 hour to 2 hours to 4 hours to 8 hours to 16 hours to 24 hours. In certain embodiments at least 50% (preferably at least 75%, at least 90%, at least 95% or more) of the soluble material is removed within 12 hours (preferably within 8 hours, within 4 hours, within 2 hours, or less).

As discussed below, in certain embodiments, the cross-sectional area occupied by the soluble material may vary along the length of the devices of the invention, for example, increasing by 10% to 25% to 50% to 100% to 200% or more between two points along the length of the device. Subsequent to removal of the soluble material, the flexibility of the device may consequently vary along the length of the device.

Moreover, the formation of channels 19d may increase the drainage capabilities of the device. In this regard, it is believed that significant drainage occurs on the outside surfaces of ureteral stents, with some theories asserting that as much or more drainage occurs on the outside of stents as occurs through the central lumen 101.

Of course myriad other channel cross sections besides the semicircular channel cross-sections of FIG. 3C are possible, just a few of which are shown in FIGS. 11A-11C, specifically, triangular, rectangular and trapezoidal cross-sections, respectively, may be employed for the channels 19d, among many other shapes.

In certain embodiments, the depressions may be formed on the inside surface of the medical devices. For example, referring now to the schematic cross-section of FIG. 3D, the soluble material 19 may be formed on the inside surface of the stent 10, associated with lumen 101.

In some embodiments, an outer layer 20 (e.g., a lubricious layer, a semi-permeable sheath, etc.) may be provided at the outside surface of the device 10, as illustrated in FIG. 3E.

Figure 4A:
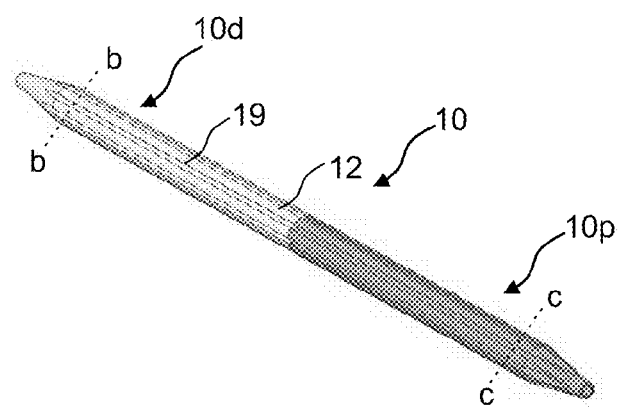
FIG. 4A is a schematic perspective view of a ureteral stent, in accordance with an embodiment of the invention.

Referring now to the embodiment of the invention illustrated in the schematic perspective view of FIG. 4A, a medical device 10, such as a ureteral stent, is illustrated, having a proximal end 10p and a distal end 10d. Like other illustrations herein, this illustration is schematic in nature (e.g., the device shown is compressed in length, relative to an actual ureteral stent, etc.). The device 10 contains an elongate tubular body 12. Along the length of the device 10 are channels filled with soluble material 19.

Figure 4B:
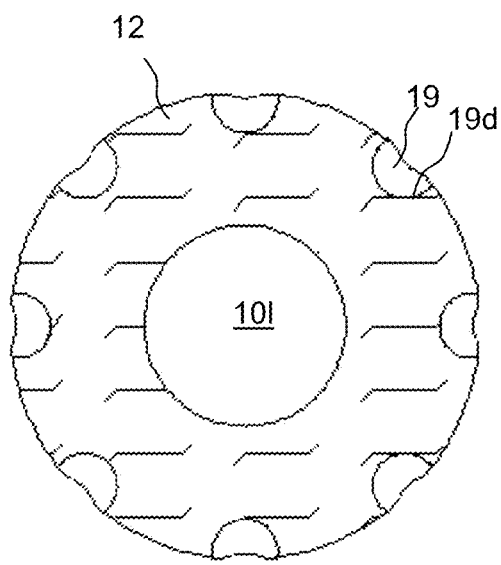
FIG. 4B is a schematic cross-sectional view taken along line b-b of FIG. 4A, in accordance with an embodiment of the invention.
Figure 4C:
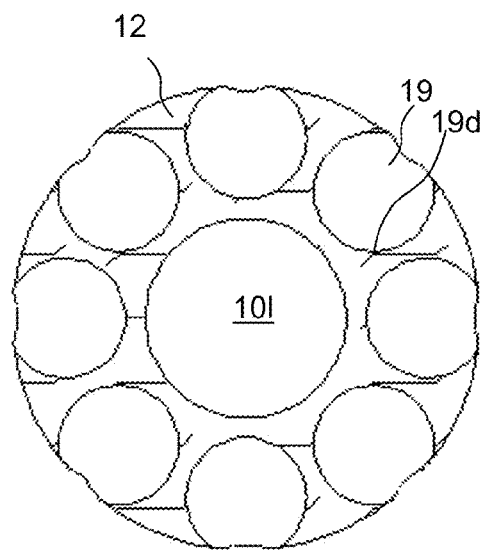
FIG. 4C is a schematic cross-sectional view taken along line c-c of FIG. 4A, in accordance with an embodiment of the invention.

As with the device of FIGS. 3A-3C, upon removal of the soluble material 19, channels are formed, which may increase the drainage capabilities of the device. In addition, upon removal of the material 19, the flexibility of device, and thus patient comfort, may be increased. As seen by comparing the distal cross-section of FIG. 4B with the proximal cross-section of FIG. 4C, the channels 19d filled with soluble material 19 are smaller at the distal end 10d of the device 10, relative to the proximal end 10p. Consequently, more material is removed from the proximal end of the device 10, which may render the proximal end 10p of the device more flexible than the distal end 10d. (Alternatively, the cross-section area of the channels 19d may be constant as one proceeds from the proximal end 10p to the distal end 10d of the device 10.)

Figure 5:
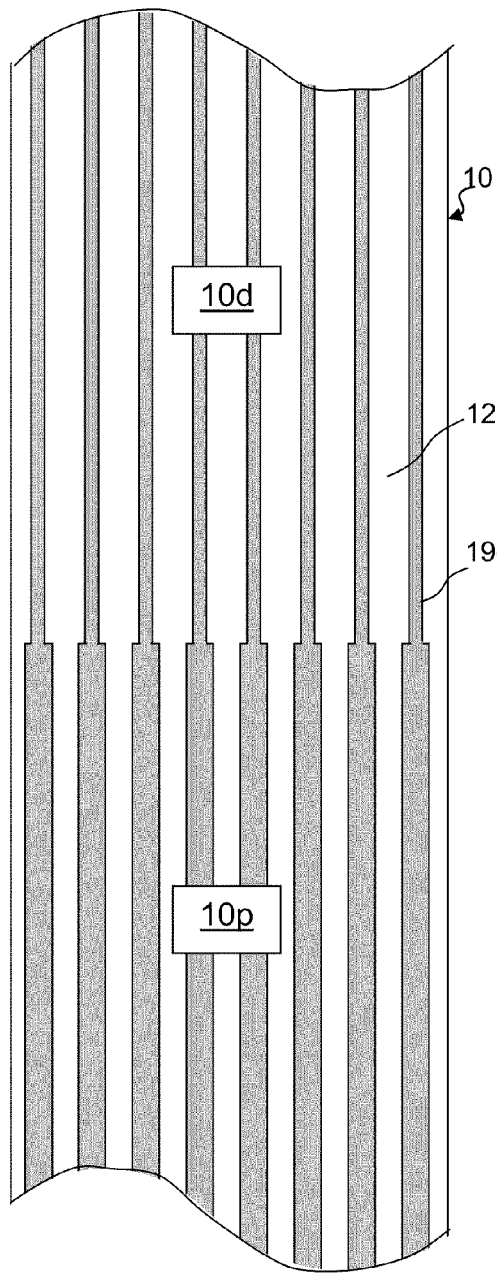
FIG. 5 is a schematic flat view of the exterior of a portion of the length of a ureteral stent, in accordance with an embodiment of the invention.
Figure 6:
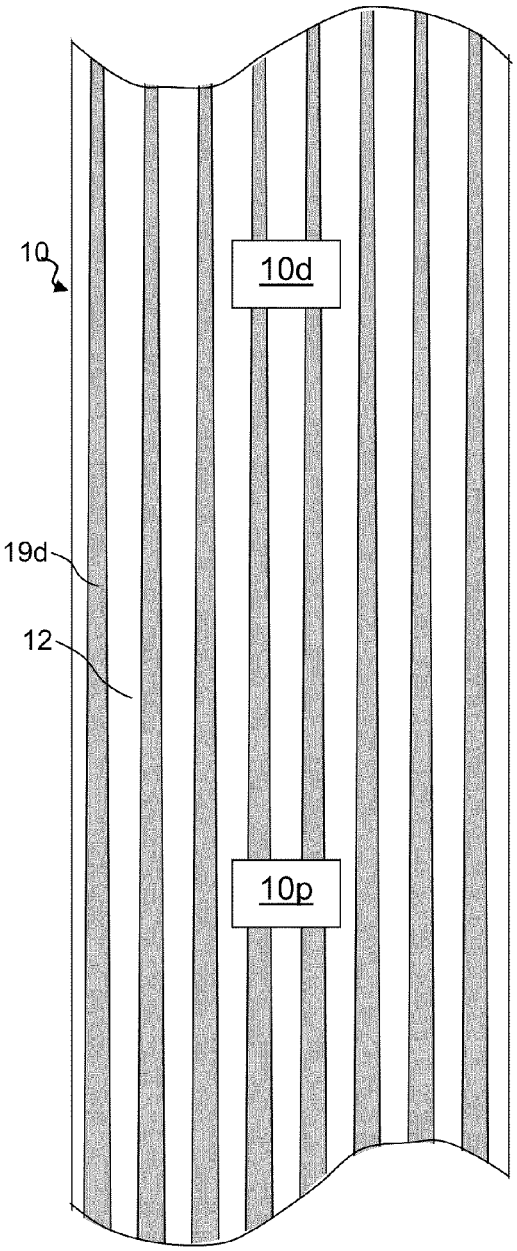

FIG. 5 is a schematic flat view (the flat view is what is observed if one were to cut the wall of the tubular device longitudinally and spread it into a flat sheet) of the exterior of a portion of the length of a ureteral stent similar to that of FIG. 4A, after removal of the soluble material. As seen from the flat view of FIG. 5, the depressions 19d (in this embodiment, channels) may decrease abruptly (stepwise) in size as one proceeds from the proximal end 10p to the distal end 10d of the device. FIG. 6 is similar to FIG. 5, except that the depressions 19d decrease gradually in size.

A change in depression cross-section may be implemented, for example, by a change in width, depth, or both. A change in depression size may also involve a complete change in the cross-sectional geometry of the depression.

Figure 7:
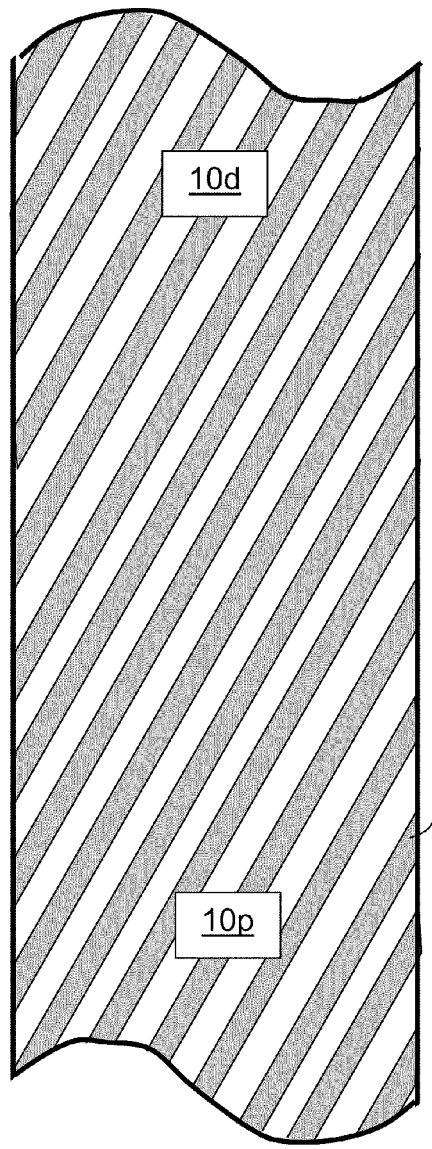
Figure 8:
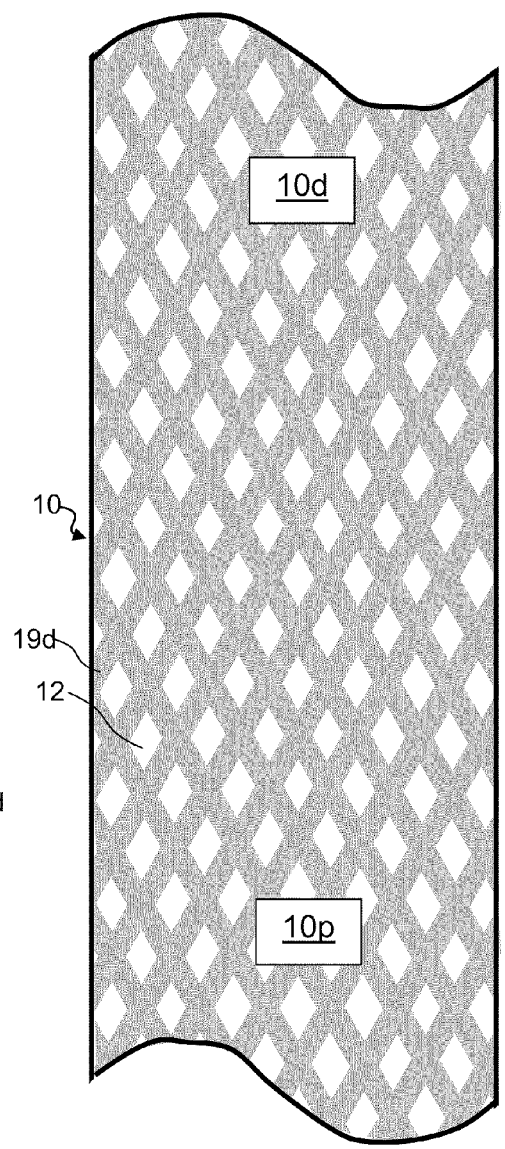

Myriad other configurations for the depressions 19 are possible. For example, the depressions 19 in the flat view of FIG. 7 are in the form of helical channels that wind around the device 10. In the flat view of FIG. 8, the cylindrical medical device 10 contains two sets of helical channels, one winding clockwise around the device, and the other winding counterclockwise. In these embodiments, the sizes of the channels 19 are constant as one proceeds from the proximal end 10p to the distal end 10d of the device 10, but this need not be the case.

In FIG. 9, the depressions 19d are not in the form of channels, but rather are in the form of indentations 19d. Because the indentations 19d (assuming that the indentations are geometrically similar) at the proximal end 10p of the device occupy more cross-sectional area than those at the distal end 10d, upon removal (or softening) of the material filling the channels, the proximal end 10p of the device may be rendered more flexible than the distal end 10d.

Thus, as with the channels discussed above, indentations 19d such as those of FIG. 9 may come in various shapes and sizes. Examples include indentations whose lateral dimensions are circular (see, e.g., the circular indentation 19d of FIG. 12A and the oval indentation 19d of FIG. 12B), and those whose lateral dimensions are polygonal (see, e.g., the rectangular indentations 19d of FIG. 9, the triangular indentation 19d of FIG. 12C and the pentagonal indentation 19d of FIG. 12D), among many other possibilities. Multiple indentations can be provided in a near infinite variety of arrays (e.g., in a linear pattern down the length of the device, in a spiral pattern, etc.).

Indentations, like channels, may also have a variety of cross sections. For example, the cross-sections of the depressions 19d shown in FIGS. 11A-11C may correspond to alternative cross sections that may be taken, for example, along line a-a of FIG. 9, among other possibilities.

Depressions may also extend through the body of the medical device, for instance, in the form of through-holes, slots, and so forth. In this regard see, for example, FIG. 10A, which is a schematic flat view of a tubular medical device 10 having a body portion 12 with a plurality of depressions 19d. As seen from the cross-sectional view taken along line a-a of FIG. 10A, which is shown in FIG. 10B, and the cross-sectional view taken along line b-b of FIG. 10A, which is shown in FIG. 10C, the depressions 19d extend completely through the medical device body. Upon dissolution of a soluble material filling the depressions 19d, multiple side ports, analogous to those of FIG. 1, will be created. Moreover, because the depressions 19d occupy more cross-sectional area at the proximal end 10p of the device 10, as compared to the distal end 10d of the device 10, upon removal (or softening) of the material filling the depressions 19d, the proximal end 10p of the device may be rendered more flexible than the distal end 10d.

As with channels, the depressions may vary gradually in size along the length of the device. On the other hand, they need not vary at all along the device length. It is also noted that where the depressions are through-holes, they may also function as side ports for the device once the soluble material is dissolved.

Although devices with hollow lumens, specifically stents, are described in detail herein, the medical devices to which the principles of the invention may be applied include essentially any implantable or insertable medical device for which an increase in flexibility, channel formation, or both, is desired shortly after implantation or insertion.

Depressions (e.g., indentations, through-holes, channels, slots, etc.) may be formed within various materials, including polymeric, metallic and ceramic materials.

Polymeric materials are particularly beneficial for the practice of the present invention and may comprise any polymer or polymer blend suitable for use in implantable or insertable medical devices. Polymers may be selected, for example, from suitable members of the following, among others: polyolefins such as polyethylenes (e.g., metallocene catalyzed polyethylenes), polypropylenes and polybutylenes; polyolefin copolymers, e.g., ethylenic copolymers such as ethylene vinyl acetate (EVA) copolymers, ethylene-methacrylic acid copolymers and ethylene-acrylic acid copolymers, where some of the acid groups can be neutralized with either zinc or sodium ions (commonly known as ionomers); vinyl aromatic polymers such as polystyrene; vinyl aromatic copolymers such as copolymers of olefins and styrene or alpha-methyl styrene, for example, butadiene-styrene copolymers and copolymers of polyisobutylene with polystyrene or polymethylstyrene, for example, polystyrene-polyisobutylene-polystyrene triblock copolymers, which are described, for example, in U.S. Pat. Nos. 5,741,331, 4,946,899, 6,545,097 and U.S. Patent Application No. 2002/0107330; polyacetals; chloropolymers such as polyvinyl chloride (PVC); fluoropolymers such as polytetrafluoroethylene (PTFE); polyesters such as polyethyleneterephthalate (PET); polyesterethers; polyamides such as nylon 6 and nylon 6,6; polyethers; polyamide ethers such as polyether block amides (PEBA) comprising (a) nylon blocks, for example, nylon 6, nylon 4/6, nylon 6/6, nylon 6/10, nylon 6/12, nylon 11 or nylon 12 blocks and (b) polyether blocks, for example, poly(ethylene oxide), poly(trimethylene oxide), poly(propylene oxide) or poly(tetramethylene oxide) blocks, one specific example of which is a poly(tetramethylene oxide)-b-polyamide-12 block copolymer, available from Elf Atochem as PEBAX; polyoctenamers such as Vestenamer® from Degussa Corp., Parsippany, N.J., which is a mixture of cyclic and linear polyoctenamers; elastomeric and thermoplastic polyurethanes, including polyurethane copolymers (including block and random copolymers that are polyether based, polyester based, polycarbonate based, aliphatic based, aromatic based and mixtures thereof), commercially available examples of which include Carbothane®, Tecoflex®, Tecothane®, Tecophilic®, Tecoplast®, Pellethane®, Chronothane® and Chronoflex®); and vinyl aromatic polymers and copolymers; silicones; polycarbonates; as well as mixtures of any of the foregoing, among others.

EVA copolymers are one preferred group polymers for use in ureteral stents. Examples include EVA copolymers having a vinyl acetate content of from about 5% to about 40% (including 5% to 10% to 15% to 20% to 25% to 30% to 35% to 40%, with 10-30% being typical). Increasing the vinyl acetate content typically results in a softer material, while decreasing the vinyl acetate content typically produces a harder material.

Soluble materials for filling depressions in accordance with the invention may be selected, for example, from suitable members of the following: polyethylene glycol (also known as polyoxyethylene), polyalkylene oxides including polyethylene oxide and polyethylene oxide-polypropylene oxide copolymers (also known as poloxamers), polyhydroxyethylmethacrylate, polyvinylpyrrolidone, polyacrylamide and its copolymers, sugars, polysaccharides including cyclodextrins and dextran, and soluble celluloses, for example, ionic celluloses such as sodium carboxymethyl cellulose, and non-ionic celluloses, for example, hydroxyalkyl celluloses such as hydroxymethyl cellulose, hydroxyethyl cellulose, and hydroxyproyl cellulose (e.g., Klucel G and Klucel E), and blends of the same, among others.

The medical device of the present invention may also contain one or more optional additives, for example, selected from therapeutic agents, radio-opacifying agents, pigments, other optional additives such as plasticizers and extrusion lubricants, and combinations of the above, among others, in amounts effective to serve their intended purposes. Where used in the devices of the invention, such optional additives may be present, for example, (a) in polymeric materials such as those discussed above, among others, (b) in soluble materials such as those discussed above, among others, (c) in both polymeric and soluble materials.

Examples of optional therapeutic agents include antimicrobial agents and agents that reduce pain and discomfort, such as anti-inflammatory agents, analgesic agents, local anesthetic agents, antispasmodic agents, and combinations thereof While these may be delivered systemically (e.g., orally or by injection), therapeutic agent administered locally for a site-specific therapeutic purpose require significantly lower doses than oral administration of the same drug for the same purpose. An advantage of the lower doses used in site-specific delivery is that unwanted or even toxic side affects of systemic concentrations of the same drug may be avoided.

As indicated above, optional therapeutic agents, if any, may be provided, for example, within soluble material regions (e.g., for quick release), within depression-containing polymeric regions (e.g., for more sustained release), or both, among other possibilities.

Thus, in certain embodiments (e.g., where a therapeutic agent is provided within a polymeric material), the device may exhibit an extended release profile. By "extended release profile" is meant a release profile by which an effective amount of therapeutic agent continues to be released at least one day 1 after device implantation or insertion, for example, from 1 day to 2 days to 4 days to 1 week to 2 weeks to 1 month to 2 months to 6 months to 1 year or more after device implantation.

In certain embodiments (e.g., where a therapeutic agent is provided within a soluble material), the device may exhibit a rapid release profile. By "rapid release profile" is meant a release profile by which the therapeutic agent is substantially all released (e.g., 75% to 90% to 95% or more is released) within 24 hours of implantation or insertion, for example, from 1 hour or less to 2 hours to 4 hours to 8 hours to 16 hours to 24 hours.

In certain embodiments of the invention, the soluble material regions are configured to be as absorbent as possible (e.g., by forming them from a material that is swellable, porous, etc.), thereby enhancing the ability of these regions to take up one or more optional agents. For example, the soluble material may be formed from a powder or from a slurry to provide a porous structure that is capable of absorbing therapeutic agents or other optional agents.

In certain embodiments, prior to insertion or implantation, one (e.g., a physician or an assistant to the same) may spray the device with, or dip the device into, a therapeutic-agent-containing solution, thereby loading the device with a drug of choice.

The term "antimicrobial agent" as used herein means a substance that kills and/or inhibits the proliferation and/or growth of microbes, particularly bacteria, fungi and yeast. Antimicrobial agents, therefore, include biocidal agents and biostatic agents as well as agents that possess both biocidal and biostatic properties. In the context of the present invention, the antimicrobial agent kills and/or inhibits the proliferation and/or growth of microbes on and around the surfaces of an implanted medical device, and can therefore inhibit biofilm formation (encrustation) in some cases. In this regard, it is noted that as the soluble material is dissolved out of the depressions, it will carry any encrustation with it. Hence, in this respect, the devices of the present invention are "self cleaning."

Antimicrobial agents may be selected, for example, from triclosan, chlorhexidine, nitrofurazone, benzalkonium chlorides, silver salts and antibiotics such as rifampin, gentamycin and minocyclin and combinations thereof, among others. In certain embodiments, antimicrobial agents may include triclosan, chlorhexidine and salts or combinations thereof.

Anti-inflammatory agents include steroidal and non-steroidal anti-inflammatory agents. Examples of non-steroidal anti-inflammatory drugs include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

In certain embodiments, therapeutic agents for reducing pain or discomfort may be selected from ketorolac and pharmaceutically acceptable salts thereof (e.g., the tromethamine salt thereof, sold under the commercial name Toradol®), 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropan®), and combinations thereof.

The amount of therapeutic agent present, will depend, for example, upon the efficacy of the therapeutic agent employed, the release rate, and so forth. One skilled in the art can readily determine an appropriate therapeutic agent loading to achieve the desired outcome.

Radio-opacifying agents facilitate viewing of the medical device during insertion of the device and at any point while the device is implanted. A radio-opacifying agent typically functions by scattering x-rays. The areas of the medical device that scatter the x-rays are detectable on a radiograph. Among radio-opacifying agents useful in the medical device of the present invention are included bismuth salts such as bismuth subcarbonate, bismuth oxychloride, bismuth trioxide, barium sulfate, tungsten, and mixtures thereof, with bismuth salts typically being preferred. Where present, the radio-opacifying agent is typically present in an amount of from about 10% to about 40% (including 10% to 15% to 20% to 25% to 30% to 35% to 40%, with 15-30% being more typical). One skilled in the art can readily determine an appropriate radio-opacifying agent content to achieve the desired visibility.

As indicated above, in some embodiments, the devices of the invention are optionally provided with lubricious layers. Moreover, the devices of the present invention may be provided with semi-permeable sheaths in certain embodiments. For instance, a sheath may be provided which is not permeable to the material forming the soluble region(s) of the device, for example, one or more soluble polymers, but which is permeable to relatively small molecules, for example, various therapeutic agents such as those set forth above, among others. Examples of sheath materials include, for example, lipid bilayers, among other materials. Lipid bilayers can be semipermeable, selectively letting certain types of molecules pass through, for instance fats or positively charged ions. Various other types of semipermeable materials are known as well, including those used in conjunction with reverse osmosis, dialysis and other sampling and purification techniques. These embodiments of the invention may allow, for example, the device to be loaded with a therapeutic agent (e.g., by immersing the device in a solution of the agent), without loss of the soluble material. Consequently, the device may be loaded by a physician in his or her office, with a drug of his or her choice. As the soluble material subsequently dissolves (after device implantation/insertion and sheath removal), the therapeutic agent is released into the patient.

Numerous techniques are available for forming medical devices in accordance with the present invention. For example, where one or more polymers are used to form a polymeric region, and at least one of those polymers have thermoplastic characteristics, a variety of thermoplastic processing techniques may be used to form the polymer region, including extrusion techniques (for example, extrusion, coextrusion, multi-layer extrusion, multi-lumen extrusion, and so forth) and molding techniques (for example, rotational molding and injection molding including co-injection or sequential injection molding technology such as laminar injection molding, LIM, technology, where multilayer structures are desired), among others.

For example, using the above techniques, a polymeric device body can be formed, a polymeric layer can be formed onto a pre-existing device body, or a polymeric layer may be co-formed along with an underlying device body, among other possibilities.

Co-extrusion may also be employed in certain embodiments, for example, where an extruded polymeric device body, or a coating of the same, is formed whose properties vary axially, for example, in polymer content or in optional agent content or concentration. For instance, melts producing polymeric regions of different durometer value may be extruded according to a stepwise change or a gradient to form a device, such as a stent, with opposing end regions having different polymer contents, and an abrupt or gradual transition region in between. Various extrusion techniques have been described for these purposes, including, for example, interrupted layer co-extrusion (ILC). For further information, see, for example, the extrusion processes described in U.S. Pat. Nos. 5,622,665 and 6,508,805, which are hereby incorporated by reference. By virtue of the ILC process, an extrusion may be formed in which a relatively soft (low durometer) polymer section transitions to a relatively hard (high durometer) polymer section.

Regardless the type of extrusion employed, depressions may be created in the extruded polymeric region at the time of formation, for example, by selection of an appropriately configured extrusion die.

Depressions may also be created in a polymeric region at the time of formation using other techniques, including non-extrusion based thermoplastic techniques and solvent based techniques, for example, through the use of an appropriately configured mold.

Depressions may also be created subsequent to formation of the polymeric region, for example, by machining or another suitable technique.

If an optional additive is to be provided within the polymeric device body or portion thereof, and if the additive is stable under processing conditions, then the additive may be combined with the polymer(s) forming the polymeric region prior to processing. If not, then the additive may nonetheless be added to an already formed polymeric region, for example, by spraying or imbibing with a solution containing an appropriate additive.

In some embodiments, processing may comprise dry blending, compounding or otherwise mixing one or more polymers and one or more optional additives to form a relatively homogeneous mixture thereof and then forming the polymeric device body or portion thereof from the homogenous mixture. Mixing or compounding polymer(s) with one or more optional additives to form a relatively homogeneous mixture thereof may be performed with any device known in the art and useful for mixing polymeric materials with additives. Where the polymer(s) are thermoplastic in nature, the additives may be mixed with the polymer(s) while in a melt stage to form a relatively homogenous mixture. A common way of doing so is to apply mechanical shear to a mixture of the polymer(s) and optional additives. Devices in which the polymer and additives may be mixed in this fashion include, for example, devices such as a single screw extruder, a twin screw extruder, a banbury mixer, a high-speed mixer, and a ross kettle. Mixing may also be achieved by dissolving polymer(s) of interest with one or more optional additives in a suitable solvent system.

As a specific example, a ureteral stent may be formed, which contains (a) a therapeutic agent (b) a radio-opacifying agent, (c) a colorant and (d) the balance ethylene vinyl acetate (EVA) copolymer (e.g., Elvax 460, from DuPont). First, the therapeutic agent, radio-opacifying agent and colorant may be pre-blended to produce a consistent, homogenous powder blend. The pre-blended mixture may then be compounded with the EVA copolymer and extruded into pellets, which are then extruded into tubes of an appropriate diameter. For further details on extrusions of this type, see, e.g., U.S. Patent Application Publication No. 2003/0153983 to Kathleen M. Miller et al.

In accordance with the present invention, depressions may be created in such a tubular structure. Depressions may be created, for example, either during the extrusion (e.g., with an appropriately shaped extrusion die) or subsequent to extrusion (e.g., using an appropriate machining technique).

As to providing the depressions with soluble material, where the soluble material has thermoplastic character, the soluble regions may be co-formed with the polymeric depression-containing polymeric regions, for example, via coextrusion.

In other embodiments, the soluble material is provided within the depressions by filling the depressions with the soluble material, for example, using one of the following techniques, among others: (a) by compressing a powder of the soluble material into the mold, heating as needed to consolidate the same, (b) by loading a slurry of the soluble material into the depressions, followed by drying of the slurry either passively (e.g., by evaporation) or actively (e.g., by heating), (c) by loading a solution of the soluble material into the depressions, followed by active or passive drying, and (d) by loading a melt of the soluble material into the depressions, followed by active or passive cooling.

For instance, a slurry or melt of the soluble material may be provided within a bath or reservoir through which the device body (e.g., with its grooves, slots, holes, or other depressions) is pulled. The soluble material may be packed into the depressions by drawing the body through an orifice (e.g., where the depressions are on the exterior of the body) or over a mandrel (e.g., where the depressions are on the interior of the body), either of which may or may not be tapered to enhance loading of the soluble material.

In embodiments of the invention where a ureteral stent with anchoring loops (pigtails) is formed, a straightening member (e.g., a rod) may be temporarily provided, if desired, for purposes of creating the depressions, filling the depressions, etc.

As a specific example, an extruded tube formed in accordance with U.S. Patent Application Publication No. 2003/0153983 (briefly summarized above) may subsequently be cut, provided with a tapered tip, annealed, machined to form depressions (e.g., longitudinal channels, side ports if desired, etc.), heat-treated for pigtail formation, straightened with a straightening member, depressions filled with soluble material (e.g., the longitudinal channels and optionally the side ports, if present, may be filled), and a suture added.

Once a medical device is formed, it is typically packaged and sterilized. Implantable or insertable medical devices are commonly sterilized by exposure to ethylene oxide or to radiation. For example, the medical device may be placed in a foil pouch, which is either evacuated or is provided with an inert atmosphere (e.g., an atmosphere of nitrogen and/or noble gases such as argon, etc.), and the pouch is subsequently exposed to electron beam radiation as is known in the art.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An elongate medical device configured for at least partial implantation or insertion into a subject, said medical device being a ureteral stent having a proximal bladder end and a distal kidney end that comprises an elongate tubular body comprising a surface that comprises a plurality of depressions that are at least partially filled with a soluble material that is removed after implantation or insertion, thereby increasing flexibility of device, wherein the depressions occupy more cross-sectional area at the proximal end as compared to the distal end, such that the proximal end is rendered more flexible than the distal end upon removal of the soluble material.

2. The medical device of claim 1, wherein said depressions are in the form of channels that run along the length of said device.

3. The medical device of claim 1, wherein at least 50% of the soluble material is removed 12 hours after implantation or insertion.

4. The medical device of claim 1, wherein at least 90% of the soluble material is removed 4 hours after implantation or insertion.

5. The medical device of claim 1, wherein said soluble material comprises a soluble polymer.

6. The medical device of claim 5, wherein said soluble polymer is a soluble cellulose.

7. The medical device of claim 1, wherein said depression is formed within a polymeric material.

8. The medical device of claim 7, wherein said polymeric material comprises a polymer selected from ethylene vinyl acetate copolymer and silicone.

9. The medical device of claim 8, wherein the polymeric material forms said body of said medical device.

10. The medical device of claim 8, wherein said polymeric material is in the form of a layer that is disposed over an underlying medical device body.

11. The medical device of claim 1, wherein an outer surface of said stent comprises said plurality of said depressions.

12. The medical device of claim 11, wherein said depressions comprise a plurality of channels which extend along the length of the stent.

13. The medical device of claim 11, wherein said depressions comprise a plurality of channels which extend along the length of the stent in a linear fashion.

14. The medical device of claim 11, wherein said depressions comprise a plurality of channels which extend along the length of the stent in helical fashion.

15. The medical device of claim 11, wherein said depressions comprise a plurality of intersecting channels.

16. The medical device of claim 12, wherein the total cross-sectional area of the channels increases by at least 50% along the length of the stent.

17. The medical device of claim 16, wherein said increase is gradual.

18. The medical device of claim 16, wherein said increase is stepwise.

19. The medical device of claim 11, wherein said depressions comprise a plurality of holes which extend partially or completely through the wall of the stent.

20. The medical device of claim 11, wherein a polymeric material forms a body of the stent and wherein the durometer of said polymeric material varies between the distal and proximal ends of the stent.

21. The medical device of claim 1, further comprising a therapeutic agent.

22. The medical device of claim 21, wherein the soluble material comprises said therapeutic agent.

23. The medical device of claim 22, wherein more than 90% of the therapeutic agent is released within 4 hours.

24. The medical device of claim 21, wherein said therapeutic agent is selected from antimicrobial agents, agents that reduce pain and discomfort, and combinations thereof.

25. The medical device of claim 21, wherein said therapeutic agent is selected from triclosan, ketorolac, oxybutynin, and salts and combinations thereof.

26. The medical device of claim 1, further comprising a semi-porous sheath over said surface.

27. The medical device of claim 26, wherein said soluble material comprises a soluble polymer.

28. The medical device of claim 26, wherein said soluble material is porous.

29. The medical device of claim 1, wherein the depressions vary gradually in size along the length of the medical device.

30. The medical device of claim 1, wherein the depressions vary stepwise in size along the length of the medical device.

* * * * *